United States Patent [19]

Shimizu et al.

[11] Patent Number: 5,492,982
[45] Date of Patent: Feb. 20, 1996

[54] PROCESS FOR POLYMERIZATION IN VESSEL WITH COATING OF POLYMER SCALE PREVENTIVE AGENT

[75] Inventors: Toshihide Shimizu; Mikio Watanabe, both of Kamisu, Japan

[73] Assignee: Shin-Etsu Chemical Co., Ltd., Tokyo, Japan

[21] Appl. No.: 341,917

[22] Filed: Nov. 16, 1994

[30]     Foreign Application Priority Data

Nov. 16, 1993  [JP]  Japan .................................. 5-309883

[51] Int. Cl.$^6$ ........................................................ C08F 14/06
[52] U.S. Cl. ................................................. 526/62; 526/74
[58] Field of Search ..................................... 526/62, 74

[56]                  References Cited

U.S. PATENT DOCUMENTS

| | | | |
|---|---|---|---|
| 3,975,285 | 8/1976 | Ohnishi et al. | 252/299 |
| 4,757,124 | 7/1988 | Koyanagi et al. | 526/74 |
| 4,970,278 | 11/1990 | Komabashiri et al. | 526/62 |

FOREIGN PATENT DOCUMENTS

| | | |
|---|---|---|
| 0496349A1 | 7/1992 | European Pat. Off. . |
| 0632058A1 | 1/1995 | European Pat. Off. . |

OTHER PUBLICATIONS

J. Chem. Res., Synop., (2 pages) 70–71, 1992 "New convenient synthesis of 2,2'–binaphthyl–1,4:1',4'–diquinones".
Annex to the European Search Report on European Patent Application No. EP 94 11 8056.

*Primary Examiner*—Joseph L. Schofer
*Assistant Examiner*—Tom Weber
*Attorney, Agent, or Firm*—Sughrue, Mion, Zinn, Macpeak & Seas

[57]                  ABSTRACT

A process for producing a polymer of a monomer having an ethylenically unsaturated double bond is described, wherein the monomer is polymerized in a polymerization vessel having a coating on its inner wall surfaces of a specific three-component polymer scale preventive agent, these three components are a naphthoquinone dimer, a water soluble polymer, and an inorganic colloid, whereby polymer scale is prevented from being deposited on the inner wall surfaces of the polymerization vessel.

8 Claims, No Drawings

1

PROCESS FOR POLYMERIZATION IN VESSEL WITH COATING OF POLYMER SCALE PREVENTIVE AGENT

BACKGROUND OF THE INVENTION

1. Field of the Invention

The present invention relates to a polymer scale preventive agent for use in polymerization of a monomer having an ethylenically unsaturated double bond, and a process for producing a polymer using the same.

2. Description of the Prior Art

Heretofore, methods for polymerization of a monomer having an ethylenically unsaturated double bond have been known, such as suspension, emulsion, solution, gas phase and bulk polymerization processes and the like. In any of these polymerization processes, polymer scale is liable to be deposited on the areas with which the monomer comes into contact, such as inner walls, stirring equipment and so on of a polymerization vessel.

The deposition of the polymer scale results in disadvantages that the yield of the polymer and cooling capacity of the polymerization vessel are lowered, and that the polymer scale may peel off and mix into a polymeric product, thereby impairing the quality of formed products obtained by processing the polymeric product. In addition, removal of deposited polymer scale is very laborious and time-consuming. Further, the polymer scale contains unreacted monomers and, therefore, may cause physical disorders in the operators, which has been a very serious problem in recent years.

For preventing polymer scale deposition on the polymerization vessel inner wall and so forth, methods have been known, for example, a method in which a polymer scale preventive agent comprising a polar organic compound such as amine compounds, quinone compounds, aldehyde compounds, etc. is applied to the polymerization vessel inner wall and so on to form a coating and a method in which such compounds are added to an aqueous medium in which suspension polymerization is carried out (Japanese Patent Publication (KOKOKU) No. 45-30343, as practiced in some instances of suspension polymerization of vinyl chloride.

However, these methods have the disadvantage that, although the polymer scale preventive effect is exhibited while polymerization is repeated for up to about 5 or 6 batches, the effect diminishes if the number of repeated batches of polymerization exceeds 5 or 6 (that is, the scale preventive effect is poor in durability). The disadvantage is emphasized particularly where a water-soluble catalyst is used for polymerization, and, in this point, the polymer scale prevention according to these methods is unsatisfactory industrially.

For overcoming the above disadvantage, Japanese Preexamination Patent Publication (KOKAI) No. 53-13689 proposes a method in which the inner wall, etc. of a polymerization vessel are coated with a polymer scale preventive agent comprising a condensation product of an aromatic amine compound as an effective constituent. Where the polymer scale preventive agent is applied to the areas with which monomers come into contact, such as the inner wall surface of a polymerization vessel, and a coating is thereby formed, it is possible to repeat about 100 to 200 batches of polymerization without causing deposition of polymer scale on the areas located in the liquid-phase region inside the polymerization vessel. Besides, even in the above-mentioned case where a water-soluble catalyst is used, deposition of polymer scale in the liquid-phase region is similarly prevented.

However, after the coating of the polymer scale preventive agent comprising a condensation product of an aromatic amine compound as its effective constituent is formed, there still remains a drawback that polymer scale deposition may occur on the areas around the interface between the liquid phase and the gas phase located at an upper portion of the interior of the polymerization vessel.

Once polymer scale deposition occurs on the areas around the interface between the gas and liquid phases, the deposited scale will grow gradually as polymerization runs are repeated, and at last it may peel off to be incorporated into the polymeric product. If the polymeric product with the polymer scale thus mixed therein is processed into formed products such as sheets or the like, the polymer scale causes generation of many fish eyes in the formed products, thereby lowering seriously the quality of the formed products.

Besides, the polymeric product obtained upon polymerization is required to have a high whiteness. That is, when a polymeric product is formed into a sheet or the like without any addition of a coloring agent, the resulting formed product is more or less colored and such coloration, called initial coloration, is desired to be as slight as possible. However, the aforesaid coating of the polymer scale preventive agent which contains a condensation product of an aromatic amine compound may peel off or dissolve in the polymerization mass, to be incorporated into the polymeric product; in such a case, the resulting formed products will have a lowered whiteness, i.e., a higher initial coloration.

SUMMARY OF THE INVENTION

Accordingly it is an object of the present invention to provide a polymer scale preventive agent for use in polymerization of a monomer having an ethylenically unsaturated double bond that can prevent effectively the deposition of polymer scale, not only on the areas in the liquid-phase region but also on the areas around the interface between the gas and liquid phases inside a polymerization vessel, and that makes it possible to produce a polymer having a very small number of fish eyes and slight initial coloration when processed into formed products such as sheets or the like; and a process for producing a polymer using the polymer scale preventive agent.

The present invention provides, as a means of achieving the above object, a polymer scale preventive agent for use in polymerization of a monomer having an ethylenically unsaturated double bond, comprising (A) a naphthoquinone dimer compound.

The present invention also provides a process for producing a polymer of a monomer having an ethylenically unsaturated double bond, which comprises polymerizing the monomer in a polymerization vessel having a coating on its inner wall surfaces, whereby polymer scale is prevented from being deposited, wherein said coating comprises a naphthoquinone dimer compound.

According to the present invention, deposition of polymer scale in a polymerization vessel can be effectively prevented, not only on the areas in the liquid-phase region but also on the areas around the interface between the gas phase and the liquid phase. Therefore, where polymerization is conducted by applying the present invention, the operation of removing polymer scale need not be performed every run of polymerization, and productivity is thereby improved.

In addition, the polymer obtained by application of the present invention can be processed into formed products such as sheets or the like which have very few fish eyes. Furthermore, the formed products have good quality with respect to initial coloration. More specifically, the formed products have a luminosity index (L value) in the Hunter's color difference equation described in JIS Z 8730 (1980) of, for example, 70 or more in the case of vinyl chloride polymers and 80 or more in the case of SBR.

DETAILED DESCRIPTION OF PREFERRED EMBODIMENTS (A) Naphthoquinone dimer compound The naphthoquinone dimer compound herein means (A-1) a binaphthoquinonyl compound having the formula (1):

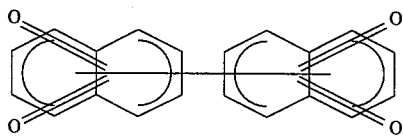

and (A-2) a binaphthoquinonyl compound wherein the two carbonyl groups of one of the naphthalene rings constituting the binaphthoquinonyl compound have been reduced into hydroxyl groups, represented by the formula (2):

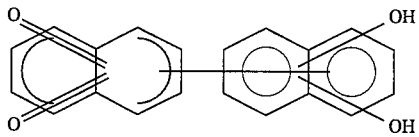

provided that the naphthoquinone dimer compound may have at least one substituent selected from the group consisting of —$NH_2$, —Cl, —Br, 13 OH, —$NO_2$, —$COCH_3$, —$OCH_3$, —$N(CH_3)_2$ and alkyl groups having 1 to 3 carbon atoms.

The compound (A-1) mentioned above includes, for example, [1,1'-binaphthalene]-3,3',4,4'-tetraone, 3' -hydroxy-[1,2'-binaphthalene]-1',3,4,4'-tetraone, [1,2'-binaphthalene] -1',3,4,4'-tetraone, 3-hydroxy-[2,2'-binaphthalene] -1,1',4,4'-tetraone, [2,2'-binaphthalene] -1,1',4,4'-tetraone and the like.

The compound (A-2) mentioned above includes, for example, 3',4'-dihydroxy-[1,1'-binaphthalene]-3,4-dione, 3,4-dihydroxy-[1,2'-binaphthalene]-1',4'-dione, 1',4' -dihydroxy-[2,2'-binaphthalene]-1,4-dione and the like.

Among the compounds (A-1) and the compounds (A-2), preferred are [2,2'-binaphthalene]-1,1',4,4'-tetraone, 1',4'-dihydroxy-[2,2'-binaphthalene]-1,4-dione, [1,1'-binaphthalene] -3,3',4,4'-tetraone, 3'-hydroxy-[1,2'-binaphthalene] -1', 3,4,4'-tetraone and 3-hydroxy-[2,2'-binaphthalene] -1,1',4, 4'-tetraone.

The naphthoquinone dimer compounds can be used singly or in combination of two or more.

The polymer scale preventive agent according to the present invention is used to form a coating on inner wall surfaces, etc. of a polymerization vessel, whereby polymer scale can be prevented from being deposited on the polymerization vessel inner wall or the like. The polymer scale preventive agent is normally used in the form of solution or dispersion, that is, as a coating liquid in forming the coating.

Preparation of Coating Liquid

To prepare the coating liquid, the naphthoquinone dimer (A) is admixed with a solvent (which will be described below), and the pH of the resulting solution is controlled to the alkaline side.

The solvent for use in preparation of the coating liquid of the present invention includes, for example, water; alcohol solvents such as methanol, ethanol, propanol, butanol, 2-butanol, 2-methyl-1-propanol, 2 -methyl-2-propanol, 3-methyl-1-butanol, 2-methyl-2-butanol, 2-pentanol and the like; ketone solvents such as acetone, methyl ethyl ketone, methyl isobutyl ketone and the like; ester solvents such as methyl formate, ethyl formate, methyl acetate, ethyl acetate, methyl acetoacetate and the like; ether solvents such as 4-methyldioxolane, ethylene glycol diethyl ether and the like; furans; aprotic solvents such as dimethylformamide, dimethyl sulfoxide, acetonitrile and the like; and so forth. These may be used either singly or as a mixed solvent of two or more thereof on a case-by-case basis.

Among the above solvents, preferred are water and mixed solvents of water and an organic solvent miscible with water. The organic solvents miscible with water include, for example, alcohol solvents such as methanol, ethanol, propanol and the like; ketone solvents such as acetone, methyl ethyl ketone and the like; and ester solvents such as methyl acetate, ethyl acetate and the like. The mixed solvents of water and an organic solvent miscible with water preferably contain the organic solvent in such an amount that there is no fear about inflammation, explosion or the like and safety in handling is ensured as to virulence, etc. Specifically, the amount of the organic solvent is preferably not more than 50% by weight, a more preferable amount being not more than 30% by weight.

The pH of the coating liquid preferably ranges from 7.5 to 13.5, more preferably from 8.0 to 13.0. For pH adjustment, alkaline compounds can be used, for example, alkali metal compounds such as LiOH, NaOH, KOH, $Na_2CO_3$, $Na_2HPO_4$ and the like, ammonium compounds such as $NH_4OH$ and the like, organic amine compounds such as ethylenediamine, monoethanolamine, diethanolamine, triethanolamine, and so forth.

Other ingredients

In order to further enhance the polymer scale preventive effect, it is preferable to add to the above-described coating liquid at least one member selected from the group consisting of (B) a water-soluble polymeric compound, (C) an inorganic colloid and (D) an alkali metal silicate.

These additives (B) to (D) enhance the scale preventive effect, presumably by interacting with the naphthoquinone dimer compound in such a manner as to improve the hydrophilicity of the surfaces being coated (in the case of the water-soluble polymeric compound (B)) or to improve adhesion of the polymer scale preventive agent to the polymerization vessel wall and so on (in the cases of the inorganic colloid (C) and the alkali metal silicate (D)).

(B) Water-soluble polymeric compound

The water-soluble polymeric compounds (B) which can be added to the polymer scale preventive agent include, for example, amphoteric polymeric compounds such as gelatin, casein and the like; anionic polymeric compounds such as polyacrylic acid, polystyrenesulfonic acid, carboxymethyl cellulose, alginic acid, and the like; cationic nitrogen-containing polymeric compounds such as polyvinyl pyrrolidone, chitosan, polyacrylamide and the like; hydroxyl group-containing polymeric compounds such as polyvinyl alcohol, hydroxyethyl cellulose, hydroxypropyl cellulose, pectin and the like; and so forth.

Among the water-soluble polymeric compounds abovementioned, preferred are gelatin, casein, polyacrylic acid, carboxymethyl cellulose, polyvinyl pyrrolidone and pectin.

The water-soluble polymeric compounds (B) may be used either singly or in combination of two or more.

The component (B) is added in an amount of normally 1 to 1000 parts by weight, preferably 5 to 200 parts by weight, per 100 parts by weight of the component (A).

(C) Inorganic colloid

The inorganic colloids (C) which can be added to the polymer scale preventive agent are those obtained by a condensing method or a dispersing method using water as a dispersion medium, with the colloidal particles ranging from 1 to 500 mμ in size.

Specifically, the applicable inorganic colloids include, for example, colloids of an oxide, a hydroxide or a mixture thereof, the oxide and hydroxide being those of a metal such as aluminum, thorium, titanium, zirconium, antimony, tin, iron and the like; colloids of tungstic acid, vanadium pentoxide, gold and silver; silver iodide sol; colloids of selenium, sulfur, silica and the like; and so forth. Among the inorganic colloids (C) above, preferred are colloids of an oxide, a hydroxide or a mixture thereof of a metal selected from the group consisting of aluminum, titanium, zirconium, tin and iron, and colloidal silica. The inorganic colloids (C) may be used either singly or in combination of two or more.

The inorganic colloids (C) are added in an amount of normally 1 to 1000 parts by weight, preferably 5 to 500 parts by weight, per 100 parts by weight of the component (A).

(D) Alkali metal silicates

The alkali metal silicates (D) include, for example, metasilicates ($M_2SiO_3$), orthosilicates ($M_4SiO_4$), disilicates ($M_2Si_2O_3$), trisilicates ($M_3Si_3O_7$), sesquisilicates ($M_4Si_3O_{10}$) and the like of alkali metals such as lithium, sodium, potassium and the like (wherein M stands for an alkali metal such as lithium, sodium and potassium); and water glass. The alkali metal silicates (D) may be used either singly or in combination of two or more.

The component (D) is added in an amount of normally 1 to 1000 parts by weight, preferably 5 to 500 parts by weight, per 100 parts by weight of the component (A).

Where the component (C) and the component (D) are used in combination, the total amount of the components (C) and (D) is preferably 1 to 1000 parts by weight, more preferably 5 to 500 parts by weight, per 100 parts by weight of the component (A).

For best improving the polymer scale preventing effect, it is preferable to use a combination of the water-soluble polymeric compound (B) with the inorganic colloid (C) or a combination of the water-soluble polymeric compound (B) with the alkali metal silicate (D). Where the components (B) and (C) are used in combination, the amount of the component (C) is preferably 5 to 3000 parts by weight, more preferably 50 to 1000 parts by weight, per 100 parts by weight of the component (B). Where the components (B) and (D) are used in combination, the component (D) is preferably used in an amount of 5 to 3000 parts by weight, more preferably 50 to 1000 parts by weight, per 100 parts by weight of the component (B).

The concentration of the component (A) in the coating liquid is not particularly limited, as long as the total coating weight described later can be obtained. Normally, the concentration of the component (A) is on the order of 0.001 to 5% by weight, a preferable concentration being on the order of 0.05 to 2% by weight. Where the components (B) to (D) are added, the total concentration of the components (A) to (D) is preferably on the order of 0.01 to 10% by weight, more preferably on the order of 0.1 to 3% by weight.

Formation of coating

To form a coating on inner wall surfaces of a polymerization vessel using the coating liquid prepared as above-described, first the coating liquid is applied to the inner wall surfaces of the polymerization vessel. Then, the applied coating liquid is dried sufficiently at a temperature ranging, for example, from room temperature to 100° C., optionally followed by washing with water.

The coating liquid is preferably applied to not only the inner wall surfaces of a polymerization vessel but also other areas with which the monomer comes into contact during polymerization, for example, stirring blades, stirring shaft, baffles, condensers, headers, search coil, bolts, nuts, etc.

More preferably, for formation of the coating, the coating liquid is applied to areas with which the monomer does not come into contact during polymerization but on which polymer scale may be deposited, for example, the inner surfaces, etc. of equipment and pipes of an unreacted monomer recovery system. Specifically, such areas include the inner surfaces of monomer distillation columns, condensers, monomer stock tanks, valves, and so on.

The method of applying the coating liquid to the inner wall surfaces of a polymerization vessel is not particularly restricted, and includes, for example, brush coating, spray coating, a method by filling the polymerization vessel with the polymer scale preventive agent followed by withdrawal thereof, and the automatic coating methods as disclosed in Japanese Pre-examination Patent Publication (KOKAI) Nos. 57-61001 and 55-36288, Japanese Patent Publication (KOHYO) Nos. 56-501116 and 56-501117, and Japanese Pre-examination Patent Publication (KOKAI) No. 59-11303, etc.

The method of drying wet coated surfaces provided by application of the coating liquid, is not restricted, either. For example, the following methods can be used: a method in which, after the coating liquid is applied, hot air with a suitable elevated temperature is blown to the coated surface; a method in which the inner wall surfaces of a polymerization vessel and the surfaces of other parts to be coated are preliminarily heated, for example, to a temperature of 30° to 80° C., and the coating liquid is directly applied to the heated surfaces; and so on. After dried, the coated surfaces are washed with water if necessary.

The coating obtained in this manner has a total coating weight after dried of normally 0.001 to 5 $g/m^2$, preferably 0.05 to 2 $g/m^2$.

The formed coating has good durability and retains the polymer scale-preventing action; therefore, the above-described coating operation may not necessarily be carried out every batch of polymerization. Accordingly, productivity is improved.

Polymerization

After the formation of the coating on the inner wall surfaces of a polymerization vessel, and preferably also on other areas with which monomer may come into contact during polymerization, etc. by the coating operation as above, polymerization is carried out in accordance with conventional procedures. That is, a monomer having an ethylenically unsaturated double bond, a polymerization initiator (catalyst), and optionally a polymerization medium such as water, etc., a dispersing agent such as suspending agents, solid dispersing agents, nonionic or anionic emulsifying agents, etc., and the like are charged into the polymerization vessel, and then polymerization is carried out according to conventional procedures.

The monomers having an ethylenically unsaturated double bond which can be polymerized by applying the process of the present invention include, for example, vinyl halides such as vinyl chloride and the like; vinyl esters such as vinyl acetate, vinyl propionate and the like; acrylic acid, methacrylic acid, and their esters and salts; maleic acid, fumaric acid, and their esters and anhydrides; diene monomers such as butadiene, chloroprene, isoprene and the like; styrene; acrylonitrile; vinylidene halides; vinyl ethers; and so forth. These monomers may be used either singly or in combination of two or more.

There are no particular restrictions on the type of polymerization to which the process according to the present invention can be applied. That is, the process of the present invention is effective in any of such polymerization types as suspension polymerization, emulsion polymerization, solution polymerization, bulk polymerization, and gas phase polymerization. Particularly, the process of the present invention is more suited to polymerizations in an aqueous medium, such as suspension polymerization and emulsion polymerization.

In the following, taking the cases of suspension polymerization and emulsion polymerization as an example, general procedures of polymerization will be described.

First, water and a dispersing agent are charged into a polymerization vessel. Subsequently, the polymerization vessel is evacuated to reduce the internal pressure to a value of 0.1 to 760 mmHg, and a monomer is then charged, whereupon the internal pressure usually takes a value of 0.5 to 30 kgf/cm$^2$.G. A polymerization initiator is charged into the vessel before and/or after charging the monomer. Subsequently, polymerization is carried out at a reaction temperature of 30° to 150° C. During the polymerization, one or more of water, a dispersing agent and a polymerization initiator may be added, if necessary. Reaction temperature during the polymerization is different depending on the kind of monomer to be polymerized. For example, in the case of polymerizing vinyl chloride, polymerization is carried out at 30° to 80° C.; in the case of polymerizing styrene, polymerization is carried out at 50° to 150° C. The polymerization may be judged to be completed when the pressure inside the polymerization vessel has fallen to a value of 0 to 7 kgf/cm$^2$.G or when cooling water which is let flow into and out of a jacket provided around the polymerization vessel has come to show approximately equal inlet and outlet temperatures (i.e., when liberation of heat due to polymerization reaction has subsided). The amounts of the water, dispersing agent and polymerization initiator to be charged for polymerization are normally 20 to 500 parts by weight, 0.01 to 30 parts by weight, and 0.01 to 5 parts by weight, respectively, per 100 parts by weight of the monomer.

In solution polymerization, an organic solvent such as toluene, xylene, pyridine, etc. is used as the polymerization medium, in place of water. A dispersing agent may be used, if necessary. The other conditions for polymerization are generally the same as those described for suspension and emulsion polymerizations.

In bulk polymerization, after a polymerization vessel is evacuated to a pressure of about 0.01 mmHg to about 760 mmHg, a monomer and a polymerization initiator are charged into the polymerization vessel, and then polymerization is carried out at a reaction temperature of −10° C. to 250° C. For example, the reaction temperature is 30° to 80° C. for polymerization of vinyl chloride, and is 50° to 150° C. for polymerization of styrene.

Where polymerization is carried out by applying the process of the present invention, it is possible to prevent polymer scale from being deposited, regardless of the materials of the inner wall, etc. of a polymerization vessel. For example, where the polymerization vessel is made of a stainless steel or other steel as well as where the polymerization vessel is a glass-lined one or the like, the polymer scale deposition can be prevented from occurring during polymerization.

Those additive materials which are conventionally added in polymerization systems can be used without any limitations. That is to say, the process of the present invention can effectively prevent polymer scale deposition in polymerization systems which may contain additive materials including, for example, polymerization initiators such as t-butyl peroxyneodecanoate, bis(2-ethylhexyl) peroxydicarbonate, 3,5,5-trimethylhexanoyl peroxide, α-cumyl peroxyneodecanoate, cumene hydroperoxide, cyclohexanone peroxide, t-butyl peroxypivalate, bis(2-ethoxyethyl) peroxydicarbonate, benzoyl peroxide, lauroyl peroxide, 2,4-dichlorobenzoyl peroxide, diisopropyl peroxydicarbonate, α,α'-azobisisobutyronitrile, α,α'-azobis-2,4-dimethylvaleronitrile, potassium peroxodisulfate, ammonium peroxodisulfate, p-menthane hydroperoxide, etc.; suspending agents comprised of, for example, natural or synthetic polymeric compounds such as partially saponified polyvinyl alcohols, polyacrylic acids, vinyl acetate/maleic anhydride copolymers, cellulose derivatives (e.g. hydroxypropyl methyl cellulose), pyrogallol-acetone resins, etc.; solid dispersing agents such as calcium phosphate, hydroxyapatite, etc.; nonionic emulsifying agents such as sorbitan monolaurate, sorbitan trioleate, polyoxyethylene alkyl ether, etc.; anionic emulsifying agents such as sodium lauryl sulfate, sodium alkylbenzenesulfonates (e.g. sodium dodecylbenzenesulfonate), sodium dioctylsulfosuccinate, etc.; fillers such as calcium carbonate, titanium oxide, etc.; stabilizers such as tribasic lead sulfate, calcium stearate, dibutyltin dilaurate, dioctyltin mercaptide, etc.; lubricants such as rice wax, stearic acid, cetyl alcohol, etc.; plasticizers such as DOP, DBP, etc.; chain transfer agents such as mercaptans (e.g. t-dodecyl mercaptan), trichloroethylene, etc.; pH adjusters, and so forth.

In addition to being used for formation of the coating on the inner wall surfaces, etc. of the polymerization vessel, the polymer scale preventive agent of the present invention may further be added directly to the polymerization medium, whereby a further enhanced effect in preventing deposition of polymer scale can be obtained. In that case, the addition amount of the agent suitably ranges from about 5 to about 1000 ppm based on the total weight of the monomer or monomers charged into the polymerization vessel. At the time of adding the polymer scale preventive agent, care should be taken not to affect adversely the fish eye, bulk specific gravity, particle size distribution or other qualities of the resulting polymeric product.

EXAMPLES

The present invention will now be described in detail below, with reference to working examples thereof and comparative examples. In the tables below, the experiments bearing a No. marked with * are comparative examples, and the other experiments, bearing a non-marked No., are working examples of the present invention.

Example 1 (Experiment Nos. 101 to 111)

In each experiment, a stainless-steel polymerization vessel having an internal capacity of 1000 liters and equipped with a stirrer was used to carry out polymerization, as described below.

In preparing a coating liquid in each experiment, the naphthoquinone dimer compound (A), water-soluble polymeric compound (B), inorganic colloid (C) and alkali metal silicate (D) set forth in Table 1 as well as the alkaline compound and solvent set forth in Table 2 were used in such amounts as to produce the total concentration of (A)+(B)+(C)+(D), weight ratio of (A):(B):(C):(D), solvent composition, and pH shown in Table 2. The inorganic colloids (a to g, in Tables 1 and 5) which were used as component (C) in this example and Example 2 described below are shown in Table 4.

In each experiment, the coating liquid prepared as above was applied to the inner wall of the polymerization vessel and to the stirring shaft, stirring blades and the like parts with which the monomer comes into contact during polymerization. The coating liquid thus applied was dried by heating at 40° C. for 15 minutes to form a coating, followed by washing with water.

Subsequently, in each experiment, polymerization was conducted as follows. The polymerization vessel provided with the coating by the coating treatment as above was charged with 400 kg of water, 200 kg of vinyl chloride, 250 g of partially saponified polyvinyl alcohol, 25 g of hydroxypropyl methyl cellulose and 70 g of 3,5,5-trimethylhexanoyl peroxide, followed by polymerization with stirring at 66° C. for 6 hours. After the polymerization was finished, the polymeric product and unreacted monomer were recovered, and the inside of the polymerization vessel was washed with water to remove residual resin.

Thereafter, the above process including the polymerization and the washing of the inside of polymerization vessel with water was repeated batchwise, without carrying out the coating operation, the repetition number of batch being given in Table 3.

After the final batch was over, in each experiment, the amount of polymer scale deposited on areas located in the liquid-phase region and that on areas around the interface between gas and liquid phases inside the polymerization vessel were determined according to the method described below. The results are given in Table 3.

Measurement of the amount of polymer scale deposited

The scale deposited in an area of 10 cm square at a predetermined location on the inner wall of a polymerization vessel is scraped off with a stainless steel spatula as completely as can be confirmed with the naked eye, and then the scraped scale is weighed on a balance. The measured value is multiplied by 100 to obtain the amount of the deposited polymer scale per area of 1 $m^2$.

Besides, the number of fish eyes appearing upon formation of a polymer into a sheet was measured with respect to the polymers obtained in the experiments, according to the method below. The results are given in Table 3.

Measurement of fish eyes

A hundred (100) parts by weight of a polymer obtained, 50 parts by weight of dioctyl phthalate (DOP), 1 part by weight of dibutyltin dilaurate, 1 part by weight of cetyl alcohol, 0.25 part by weight of titanium oxide and 0.05 part by weight of carbon black are mixed. The resulting mixture is kneaded at 150° C. for 7 minutes with 6 inch rolls, and then formed into a sheet 0.2 mm thick. The obtained sheet is examined for the number of fish eyes per 100 $cm^2$ by light transmission.

Further, measurement of luminosity index (L value) of a sheet formed from a polymer was carried out, according to the method below, with respect to the polymers produced in the experiments. The results are given in Table 3.

Measurement of luminosity index (L value)

A hundred (100) parts by weight of the obtained polymer, 1 part by weight of a tin laurate stabilizing agent (TS-101, product of Akisima Chemical Co.) and 0.5 part by weight of a cadmium stabilizing agent (C-100J, product of Katsuta Kako Co.), and 50 parts by weight of dioctyl phthalate as a plasticizer are kneaded at 160° C. for 5 minutes with a twin roll mill, and then formed into a sheet 1 mm thick. Subsequently, this sheet is placed in a mold measuring 4×4×1.5 cm, heated at 160° C. under a pressure of 65 to 70 kgf/$cm^2$ for 0.2 hour and press molded under the same conditions to prepare a test specimen. This test specimen is measured for luminosity index L in the Hunter's color difference equation described in JIS Z 8730 (1980). The greater the value of L, the higher the whiteness evaluated, namely, the slighter the initial coloration evaluated.

The value of L is determined as follows.

The stimulus value Y of XYZ color system is determined by the photoelectric tristimulus colorimetry using the standard light C, photoelectric colorimeter (Color measuring color difference meter Model Z-1001DP, product of Nippon Denshoku Kogyo K.K.) in accordance with JIS Z 8722. As the geometric condition of illumination and light reception, the condition d defined in section 4.3.1 of JIS Z 8722 is adopted. From the stimulus value Y obtained, the L value is calculated based on the equation: $L=10Y^{1/2}$ described in JIS Z 8730 (1980).

TABLE 1

| Exp. No. | (A) Naphthoquinone dimer compound | (B) Water-soluble polymeric compound | (C) Inorganic colloid | (D) Alkali metal silicate |
|---|---|---|---|---|
| 101* | — | — | — | — |
| 102 | [2,2'-Binaphthalene]-1,1',4,4'-tetraone | — | — | — |
| 103 | [2,2'-Binaphthalene]-1,1',4,4'-tetraone | — | b | — |
| 104 | [2,2'-Binaphthalene]-1,1',4,4'-tetraone | Gelatin | a | — |
| 105 | [2,2'-Binaphthalene]-1,1',4,4'-tetraone | — | — | — |
| 106 | 1'4'-Dihydroxy-[2,2'-binaphthalene]-1,4-dione | — | — | — |
| 107 | 1'4'-Dihydroxy-[2,2'-binaphthalene]-1,4-dione | Polyvinyl pyrrolidone | c | — |
| 108 | [1,1'-Binaphthalene]-3,3',4,4'-tetraone | — | — | — |
| 109 | 3'-Hydroxy-[1,2'-binaphthalene]-1',3,4,4'-tetraone | Polyacrylic acid | d | — |
| 110 | 3'-Hydroxy-[2,2'-binaphthalene]-1,1',4,4'-tetraone | — | g | — |
| 111 | 3'-Hydroxy-[2,2'-binaphthalene]-1,1',4,4'-tetraone | — | — | $Na_2SiO_3$ |

TABLE 2

| Exp. No. | Total conc. of (A) + (B) + (C) + (D) (wt. %) | (A):(B):(C):(D) (weight ratio) | Solvent (weight ratio) | Alkaline compound | pH |
|---|---|---|---|---|---|
| 101* | — | — | — | — | — |
| 102 | 0.5 | — | Water:Methanol (90:10) | NaOH | 11.5 |
| 103 | 0.5 | 100:—:100:— | Water:Methanol (80:20) | NaOH | 12.0 |
| 104 | 0.5 | 100:100:100:— | Water:Methanol (70:30) | NaOH | 12.0 |
| 105 | 0.5 | — | Dimethylformamide:Metanol (10:90) | — | — |
| 106 | 0.2 | — | Water:Methanol (90:10) | LiOH | 12.0 |
| 107 | 0.5 | 100:50:100:— | Methanol | — | — |
| 108 | 0.5 | — | Water:Methanol (10:90) | Ethylene-diamine | 11.0 |
| 109 | 0.5 | 100:100:300:— | Water:Methanol (80:20) | NaOH | 11.5 |
| 110 | 0.2 | 100:—:50:— | Water:Methanol (70:30) | NaOH | 11.5 |
| 111 | 0.3 | 100:—:—:50 | Water:Methanol (80:20) | NaOH | 11.0 |

TABLE 3

Results of Polymerization

| Exp. No. | Repetition number of batch | Polymer scale amount (g/m²) Liquid phase | Polymer scale amount (g/m²) Around interface between gas and liquid phases | Number of fish eyes | Luminosity index (L) |
|---|---|---|---|---|---|
| 101* | 1 | 320 | 1100 | 120 | 73.0 |
| 102 | 3 | 0 | 16 | 20 | 73.0 |
| 103 | 3 | 0 | 8 | 13 | 73.0 |
| 104 | 3 | 0 | 3 | 9 | 73.0 |
| 105 | 3 | 0 | 9 | 13 | 73.0 |
| 106 | 2 | 0 | 20 | 28 | 73.0 |
| 107 | 2 | 0 | 6 | 10 | 73.0 |
| 108 | 2 | 0 | 12 | 16 | 73.0 |
| 109 | 2 | 0 | 6 | 9 | 73.0 |
| 110 | 2 | 0 | 10 | 12 | 73.0 |
| 111 | 2 | 0 | 11 | 12 | 73.0 |

TABLE 4

| Inorganic colloid | Diameter of colloidal particles | Name of article | Manufacturer |
|---|---|---|---|
| a | 10–20 mµ | Snowtex O* (colloidal silica) | Nissan Chemical Industries, Ltd. |
| b | 5–7 mµ | Snowtex CXS-9* (colloidal silica) | Nissan Chemical Industries, Ltd. |
| c | 100–200 mµ | Titanium oxide | Nissan Chemical Industries, Ltd. |
| d | 10–20 mµ | Aluminum oxide | Nissan Chemical Industries, Ltd. |
| e | 60–70 mµ | Zirconium oxide | Nissan Chemical Industries, Ltd. |
| f | 20–50 mµ | Tin oxide | Nissan Chemical Industries, Ltd. |
| g | 10–15 mµ | Iron hydroxide | produced by the present inventors |

Note *: Trade name

Example 2 (Experiment Nos. 201 to 206)

In each experiment, a stainless-steel polymerization vessel having an internal capacity of 20 liters and equipped with a stirrer was used for polymerization.

In preparation of a coating liquid in each experiment, the naphthoquinone dimer compound (A), water-soluble polymeric compound (B), inorganic colloid (C) and alkali metal silicate (D) set forth in Table 5 as well as the alkaline compound and solvent set forth in Table 6 were used in such amounts as to produce the solvent composition, total concentration of (A)+(B)+(C)+(D), weight ratio of (A):(B):(C):(D), and pH given in Table 6. The coating liquid thus prepared was applied to the inner wall of the polymerization vessel and to the stirring shaft, stirring blades and the like areas with which the monomer comes into contact during polymerization. The polymer scale preventive agent applied was dried by heating at 40° C. for 15 minutes to form a coating, followed by washing the inside of the polymerization vessel with water.

Subsequently, in each experiment, polymerization was carried out as follows. The polymerization vessel provided with the coating as above was charged with 9 kg of water, 225 g of sodium dodecylbenzenesulfonate, 12 g of t-dodecyl mercaptan and 13 g of potassium peroxodisulfate. The inside atmosphere of the polymerization vessel was replaced with nitrogen gas, thereafter 1.3 kg of styrene and 3.8 kg of butadiene were charged into the vessel, and polymerization was carried out at 50° C. for 20 hours. After the polymerization was completed, the polymeric product and unreacted monomers were recovered, followed by washing the inside of the vessel with water to remove residual resin.

Thereafter, the above process including the polymerization and the washing of the inside of polymerization vessel with water was repeated batchwise, without carrying out the coating operation, the repetition number of batch being given in Table 7.

After the final batch was over, in each experiment, the amount of polymer scale deposited on areas located in the liquid-phase region and that on areas around the interface between gas and liquid phases inside the polymerization vessel were determined according to the same method as in Example 1. The results are given in Table 7.

Besides, measurement of luminosity index (L value) of a sheet formed from a polymer was carried out with respect to each of the polymers produced in the experiments, according to the method below. The results are given in Table 7.

Measurement of luminosity index (L value)

To 1 kg of the polymer latex obtained was added 1 kg of 2% magnesium sulfate solution to cause aggregation and sedimentation. The sediment was filtered off, washed with a hot water at 80° to 90° C. twice or three times and dried at 40° C. for 25 hours in a vacuum dryer to give a resin.

The resin was placed in a mold measuring 9×9×0.1 cm (depth), heated at 195° C. under a pressure of 50 to 60 kgf/cm$^2$ for 0.2 hour and press molded under a final pressure of 80 kgf/cm$^2$ to prepare a test specimen. This test specimen was measured for luminosity index L in the same manner as in Example 1.

TABLE 5

| Exp. No. | (A) Naphthoquinone dimer compound | (B) Water-soluble polymeric compound | (C) Inorganic colloid | (D) Alkali metal silicate |
|---|---|---|---|---|
| 201* | — | — | — | — |
| 202 | [2,2'-Binaphthalene]-1,1',4,4'-tetraone | — | b | — |
| 203 | [2,2'-Binaphthalene]-1,1',4,4'-tetraone | Polyacrylic acid | c | — |
| 204 | 1'4'-Dihydroxy-[2,2'-binaphthalene]-1,4-dione | Gelatin | f | — |
| 205 | 1'4'-Dihydroxy-[2,2'-binaphthalene]-1,4-dione | Sodium alginate | e | — |
| 206 | 3'-Hydroxy-[1,2'-binaphthalene]-1',3,4,4'-tetraone | Polyvinyl alcohol | — | — |

TABLE 6

| Exp. No. | Total conc. of (A) + (B) + (C) + (D) (wt. %) | (A):(B):(C):(D) (weight ratio) | Solvent (weight ratio) | Alkaline compound | pH |
|---|---|---|---|---|---|
| 201* | — | — | — | — | — |
| 202 | 0.5 | 100:—:100:— | Water:Methanol (70:30) | NaOH | 12.0 |
| 203 | 0.5 | 100:100:100:— | Methanol | — | — |
| 204 | 0.5 | 100:50:100:— | Water:Methanol (70:30) | NaOH | 12.0 |
| 205 | 0.5 | 100:50:300:— | Water:Methanol (50:50) | NaOH | 11.5 |
| 206 | 0.2 | 100:—:200:— | Water:Methanol (90:10) | Ethylenediamine | 11.5 |

TABLE 7

| | | Results of Polymerization | | |
|---|---|---|---|---|
| | | Polymer scale amount (g/m$^2$) | | |
| Exp. No. | Repetition number of batch | Liquid phase | Around interface between gas and liquid phases | Luminosity index (L) |
| 201* | 1 | 450 | 1200 | 85.0 |
| 202 | 2 | 1 | 22 | 85.0 |
| 203 | 2 | 0 | 9 | 85.0 |
| 204 | 2 | 0 | 9 | 85.0 |

TABLE 7-continued

| | | Results of Polymerization | | |
|---|---|---|---|---|
| | | Polymer scale amount (g/m$^2$) | | |
| Exp. No. | Repetition number of batch | Liquid phase | Around interface between gas and liquid phases | Luminosity index (L) |
| 205 | 2 | 0 | 8 | 85.0 |
| 206 | 2 | 1 | 30 | 85.0 |

Example 3

A stainless-steel polymerization vessel having an internal capacity of 20 liters and equipped with a stirrer was used to carry out polymerization.

The coating liquid used in Experiment No. 203 was applied to the inner wall of the polymerization vessel and to the stirring shaft, stirring blades and the like parts with which monomers come into contact during polymerization. The coating liquid applied was dried by heating at 50° C. for 15 minutes to form a coating, followed by washing of the inside of the vessel with water.

Thereafter, the polymerization vessel provided with the coating as above was charged with 4.0 kg of water and 6 g of sodium dodecylbenzenesulfonate, and temperature was raised to 60° C. with stirring. After the gas phase in the polymerization vessel was replaced with nitrogen gas, the vessel was further charged with 94 g of n-butyl acrylate, 220 g of methyl methacrylate, 5 g of acrylic acid and 5 g of methacrylic acid. Subsequently, 1 g of ammonium persulfate and 1 g of sodium hydrosulfite were charged into the polymerization vessel, and the resulting mixture in the vessel was stirred at 60° C. for 20 minutes.

Furthermore, into the polymerization vessel were added a monomeric mixture (prepared by mixing 2.1 kg of n-butyl acrylate, 4.8 kg of methyl methacrylate, 100 g of acrylic acid and 100 g of methacrylic acid), 500 g of an aqueous 1 wt. % ammonium persulfate solution, 500 g of an aqueous 1 wt. % sodium hydrosulfite solution and 2.0 kg of an aqueous 25 wt. % polyoxyethylene nonyl phenyl ether solution, evenly over a 3-hour period. After the addition was completed, the polymerization vessel was heated to 70° C. and polymerization was carried out for 2 hours.

After the polymerization was over, the resulting polymeric product and unreacted monomers were recovered, and the inside of the vessel was washed with water to remove residual resin.

Thereafter, a batch of operations from the formation of the coating through polymerization to the washing of the inside of the polymerization vessel with water as above-described was repeated 80 times. Upon the 80th batch, the amount of polymer scale deposited on areas located in the liquid-phase region and that on areas around the interface between gas and liquid phases inside the polymerization vessel were measured in the same manner as in Example 1. The measured amount of polymer scale was 0 g/m$^2$ on the areas in the liquid-phase region and 20 g/m$^2$ on the areas around the gas-liquid interface.

What is claimed is:

1. A process for producing a polymer of a monomer having an ethylenically unsaturated double bond, which comprises polymerizing the monomer in a polymerization vessel having a coating on its inner wall surfaces, whereby polymer scale is prevented from being deposited, wherein said coating comprises:

(A) a naphthoquinone dimer compound selected from the group consisting of 1,1',4,4'-tetraone, 1',4'-dihydroxy-1,4-dione, 3,3',4,4'-tetraone, 3'-hydroxy-1',3,4,4'-tetraone and 3-hydroxy-1,1',4,4'-tetraone;

(B) a water-soluble polymeric compound; and (C) an inorganic colloid.

2. The process of claim 1, wherein said polymerization is conducted as suspension polymerization, emulsion polymerization, solution polymerization, bulk polymerization, or gas phase polymerization.

3. The process of claim 1, wherein said monomer comprises at least one compound selected from the group consisting of vinyl halides; vinyl esters; acrylic acid, methacrylic acid, and their esters and salts; maleic acid, fumaric acid, and their esters and anhydrides; diene monomers; styrene; acrylonitrile; vinylidene halides; and vinyl ethers.

4. The process of claim 1, wherein the amount of the component (B) is 1 to 1000 parts by weight per 100 parts by weight of the component (A) and the amount of the component (C) is 5 to 3000 parts by weight per 100 parts by weight of the component (B).

5. The process of claim 1, wherein the coating has been formed by applying a coating liquid to the inner wall surfaces, followed by drying, said coating liquid containing the components (A), (B) and (C) dissolved or dispersed in a solvent.

6. The process of claim 5, wherein the total concentration of the components (A), (B) and (C) in the coating liquid is 0.01 to 10% by weight.

7. The process of claim 5, wherein the solvent is water or a mixed solvent of water and an organic solvent miscible with water.

8. The process of claim 5, wherein the coating liquid has a pH of 7.5 to 13.5.

* * * * *

UNITED STATES PATENT AND TRADEMARK OFFICE
CERTIFICATE OF CORRECTION

PATENT NO.   : 5,492,982
DATED        : February 20, 1996
INVENTOR(S)  : Shimizu et al It is certified that errors appears in the above-identified patent and that said Letters Patent is hereby corrected as shown below:

IN THE CLAIMS:

Column 15,

1.  A process for producing a polymer of a monomer having an ethylenically unsaturated double bond, which comprises polymerizing the monomer in a polymerization vessel having a coating on its inner wall surfaces, whereby polymer scale is prevented from being deposited, wherein said coating comprises:

(A) a naphthoquinone dimer compound selected from the group consisting of [2,2'-binaphthalene]-1,1',4,4'-tetraone, 1',4'-dihydroxy-[2,2'-binaphthalene]-1,4-dione, [1,1'-binaphthalene]-3,3',4,4'-tetraone, 3'-hydroxy-[1,2'-binaphthalene]-1',3,4,4'-tetraone and 3-hydroxy-[2,2'-binaphthalene]-1,1',4,4'-tetraone;

(B) a water-soluble polymeric compound; and (C) an inorganic colloid.

Signed and Sealed this

Eighteenth Day of June, 1996

Attest:

BRUCE LEHMAN

Attesting Officer

Commissioner of Patents and Trademarks